US00PP18149P2

(12) United States Plant Patent
Zary

(10) Patent No.: US PP18,149 P2
(45) Date of Patent: Oct. 30, 2007

(54) SHRUB ROSE PLANT NAMED 'JACWIPET'

(50) Latin Name: *Rosa hybrida*
Varietal Denomination: JACwipet

(75) Inventor: Keith W. Zary, Agoura Hills, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 123 days.

(21) Appl. No.: 11/187,340

(22) Filed: Jul. 21, 2005

(51) Int. Cl.
*A01H 5/00* (2006.01)

(52) U.S. Cl. ..... Plt./103

(58) Field of Classification Search ..... Plt./103, Plt./107, 101, 124, 144, 117
See application file for complete search history.

(56) References Cited

U.S. PATENT DOCUMENTS

PP9,650 P * 10/1996 Olesen et al. ..... Plt./103

* cited by examiner

*Primary Examiner*—Howard J. Locker
(74) *Attorney, Agent, or Firm*—Klarquist Sparkman LLP

(57) ABSTRACT

Shrub rose plant having resistance to all major fungal diseases of roses; very large flower clusters; small, glossy foliage; compact plant habit; constant flower production and ease of propagation from soft or hardwood cuttings.

1 Drawing Sheet

Genus and species: *Rosa hybrida.*
Variety denomination: 'JACwipet'.

ORIGIN OF THE INVENTION

The present invention relates to a new and distinct variety of a shrub rose plant named 'JACwipet' which was originated by me by crossing the variety 'NOAtraum' (U.S. Plant Pat. No. 7,282), with an unnamed white shrub seedling (not patented) ('POULcov' (U.S. Plant Pat. No. 10,648)× 'POULcat' (not patented)).

BACKGROUND OF THE INVENTION

The primary objective of this breeding was to produce a new rose variety having the disease resistance of the female parent combined with the compact plant, glossy foliage and large flower trusses of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Resistance to all major fungal diseases of roses.
2. Very large pyramidal clusters of 50–70 blooms.
3. Small, glossy foliage.
4. Compact plant habit.
5. Constant flower production.
6. Ease of propagation from soft or hardwood cuttings.

Asexual reproduction of this new variety by cuttings, as performed at Wasco, Calif., shows that the foregoing and all other characteristics and distinctions come true to form and are established and transmitted through succeeding propagations.

COMPARISON WITH PARENTS

The flower color of 'JACwipet' is white versus the pink color of 'NOAtraum' and has fewer petals (5 or 6 versus 15) and smaller flowers. The unnamed seedling differs in petal count (25 versus 5 or 6) and in disease resistance (susceptible versus resistance to blackspot).

COMPARISON WITH SIMILAR VARIETY

The closest variety to 'JACwipet' is 'POULemb' (U.S. Plant Pat. No. 9,650). The latter has the same petal count (5 or 6), but a lesser prickle count (few versus normal), and a spreading and arching plant habit (versus upright and compact).

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart© 2001, except where ordinary dictionary significance of color is indicated.

Parentage:

*Seed parent.*—'NOAtraum' (U.S. Plant. Pat. No. 7,282).

*Pollen parent.*—Unnamed white shrub seedling (not patented), ('POULcov' (U.S. Plant Pat. No. 10,648)× 'POULcat' (not patented).)

Observations made from January 2003 to August 2004 from plants commencing at three years of age grown in a garden environment at Somis, Calif.

FLOWER

Blooming habit: Continuous.
Bud:
*Size.*—About 6–8 mm long and 3–4 mm in diameter when the petals start to unfurl.
*Form.*—The bud form is long.
*Color.*—When sepals first divide, bud color is White Group 155B. When half blown, the upper sides of the petals are White Group 155B and the lower sides of the petals are White Group 155B.
*Sepals.*—Color: Upper surface: Green Group 143C. Lower surface: Yellow-Green Group 144A. Length: 11–13 mm. Width: 3–4 mm. Shape: Subulate. Surface texture: Upper: Canescent. Lower: Glandular. There are three normally appendaged sepals. There are two unappendaged sepals with hairy edges.
*Receptacle.*—Color: Yellow-Green Group 144A. Shape: Pear. Size: Large, long, about 3–4 mm long× 2–3 mm wide. Surface: Smooth.
*Peduncle.*—Length: Short, averaging about 5–15 mm. Surface: Glandular. Color: Yellow-Green Group 144A. Strength: Stiff, erect.
Bloom:
*Size.*—Small. Average open diameter is about 25 mm.
*Borne.*—Several together in pyramidal clusters of 50–70 blooms.
*Stems.*—Strength: Strong. Average length is about 15–20 cm with a diameter of 5–6 mm.
*Form.*—When first open: Flat. Permanence: Retains its form to the end.
*Petalage.*—Number of petals under normal conditions: 5, occasionally 6.
*Color.*—The upper sides of the inner petals are White Group 155D. The reverse sides of the inner petals are White Group 155D. The base of each petal has a very small 1 mm×1 mm Green-Yellow Group 1D color spot. The major color on the upper sides is White Group 155D.
*Variegations.*—None.
*Discoloration.*—The general tonality at the end of the first day: No change. At the end of the third day: No change. Further aging: No change.
*Fragrance.*—None.
Petals:
*Texture.*—Thin.
*Shape.*—Obelliptic.
*Surface.*—Smooth.
*Margin.*—Entire. Apex Shape: Obtuse. Base Shape: Rounded.
*Form.*—Flat.
*Arrangement.*—Imbricated.
*Petaloids.*—Number: None observed.
*Persistence.*—Petals drop off cleanly before drying.
*Lastingness.*—On the plant: Short (about 3–4 days). As a cut flower: Short (about 4–5 days).
Reproductive parts:
*Stamens.*—Number: 55–60. Length: 4–5 mm. Anthers: Length: 0.5 mm. Color: Yellow-Orange Group 23B. Arrangement: Regular around styles. Filaments: Color: Green-White Group 157D. Length: 3.5–4.5 mm. Pollen: Color: Greyed-Orange Group 167D.
*Pistils.*—Number: About 10. Length: 3 mm. Styles: Color: Yellow-Green Group 145C. Length: 2.5 mm. Stigmas: Color: Yellow-Green Group 145C. Length: 0.5 mm. Hips: Color: Yellow-Green Group 144A. Shape: Ovate. Size: 3 mm long×5 mm wide.

PLANT

Form: Shrub.
Growth: Vigorous, upright, branching, compact.
Age at maturity: Two years.
Mature plant: Height: 45 cm Width: 30 cm.
Rootstock: Own root.
Foliage: Number of leaflets on normal mid-stem leaves: 7.
*Size.*—Small. About 80 mm long×50 mm wide.
*Quantity.*—Normal.
*Color.*—New foliage: Upper side: Yellow-Green Group 146B. Lower side: Yellow-Green Group 146B. Old foliage: Upper side: Green Group 139A. Lower side: Green Group 137C.
Leaflets:
*Size.*—About 25 mm long×15 mm wide.
*Shape.*—Pointed oval.
*Base shape.*—Oblique.
*Apex shape.*—Acuminate.
*Texture.*—Leathery, glossy.
*Edge.*—Serrated.
*Serrations.*—Single.
*Petiole.*—Color: Yellow-Green Group 146D.
*Petiole rachis.*—Color: Yellow-Green Group 146D. Underside: Rough with prickles.
*Auricles.*—None.
*Stipules.*—Length: 10 mm; serrated, bearded and has glands.
*Disease resistance.*—Resistant to rust, powdery and downy mildew and blackspot under normal growing conditions.
*Pest resistance.*—Not observed.
*Vein color.*—Green Group 137C.
*Venation pattern.*—Reticulate.
Wood:
*New wood.*—Color: Yellow-Green Group 144A. Bark: Smooth.
*Old wood.*—Color: Yellow-Green Group 144A. Bark: Smooth.
Prickles:
*Quantity.*—On main canes from base: 12–14 per 15 cm of stem. On laterals from main canes: 12–14 per 15 cm of stem.
*Form.*—Hooked slightly downward.
*Length.*—2–5 mm.
*Color when young.*—Greyed-Yellow Group 161C.
*Color when mature.*—Greyed-Orange Group 166D.
Small prickles:
*Quantity.*—On main stalks: Few. On laterals: Few.
*Color when young.*—Greyed-Yellow Group 161C.
*Color when mature.*—Greyed-Orange Group 166D.
Winter hardiness: Hardy to Zone 5.

I claim:

1. A new and distinct variety of rose plant of the shrub class, substantially as herein shown and described, characterized particularly by its resistance to all major fungal diseases of roses; its very large flower clusters; small, glossy foliage; compact plant habit; constant flower production and ease of propagation from soft or hardwood cuttings.

* * * * *

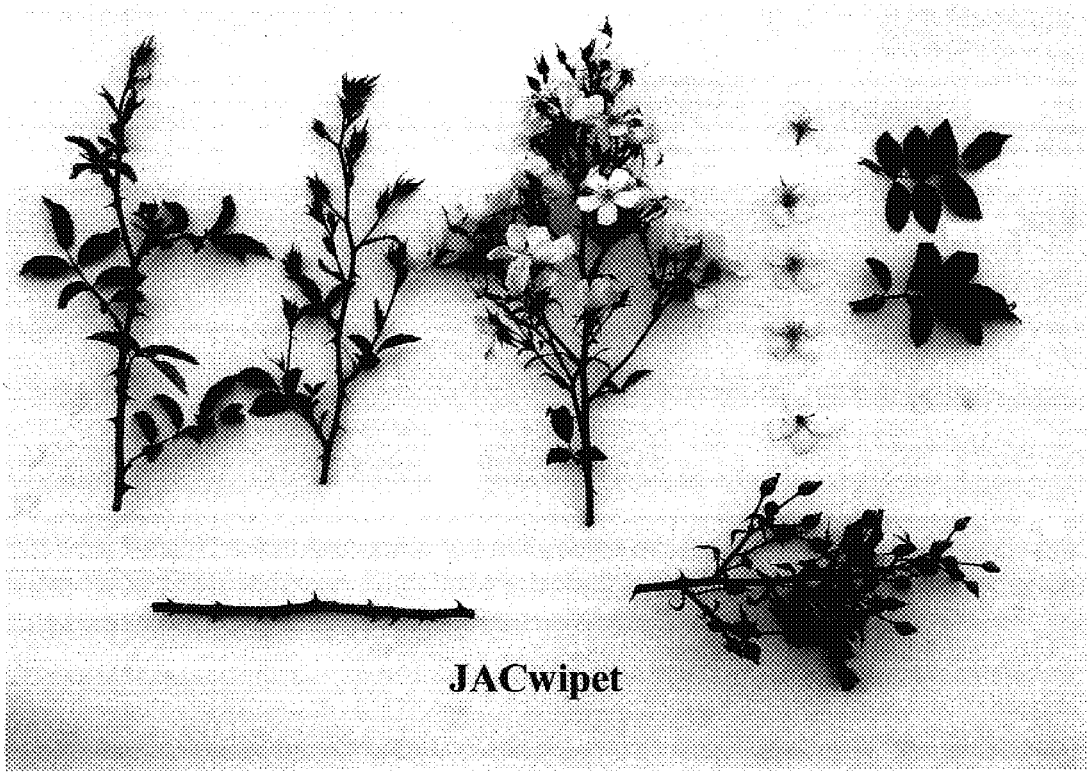
JACwipet

UNITED STATES PATENT AND TRADEMARK OFFICE

CERTIFICATE OF CORRECTION

PATENT NO. : PP 18,149 P2
APPLICATION NO. : 11/187340
DATED : October 30, 2007
INVENTOR(S) : Keith W. Zary It is certified that error appears in the above-identified patent and that said Letters Patent is hereby corrected as shown below:

In Column 1, line 33, “Easc” should read --Ease--.

In Column 2, line 2, “WITII” should read --WITH--.

In Column 4, line 12, “IIeight” should read --Height--.

In Column 4, line 48, “12 14” should read --12-14--.

In Column 4, line 50, “IIooked” should read --Hooked--.

Signed and Sealed this

Third Day of March, 2009

JOHN DOLL
*Acting Director of the United States Patent and Trademark Office*